US012001600B2

(12) United States Patent
Baldev et al.

(10) Patent No.: US 12,001,600 B2
(45) Date of Patent: Jun. 4, 2024

(54) SERVICE GLASSES WITH SELECTIVE DATA PROVISION

(71) Applicant: Beckman Coulter, Inc., Brea, CA (US)

(72) Inventors: Darshan Harish Baldev, Minneapolis, MN (US); Rebecca Jean Busacker, Chanhassen, MN (US); Jon Pallage Lindquist, Jr., Coon Rapids, MN (US); Takayuki Mizutani, Edina, MN (US); Benjamin Robert Nelson, Eden Prairie, MN (US); Cody Joseph Precord, Plymouth, MN (US)

(73) Assignee: Beckman Coulter, Inc., Brea, CA (US)

( * ) Notice: Subject to any disclaimer, the term of this patent is extended or adjusted under 35 U.S.C. 154(b) by 22 days.

(21) Appl. No.: 17/314,247

(22) Filed: May 7, 2021

(65) Prior Publication Data

US 2021/0349677 A1    Nov. 11, 2021

Related U.S. Application Data

(63) Continuation of application No. PCT/US2019/056473, filed on Oct. 16, 2019.
(Continued)

(51) Int. Cl.
*G06F 3/01* (2006.01)
*A61F 9/04* (2006.01)
(Continued)

(52) U.S. Cl.
CPC ............ *G06F 3/011* (2013.01); *A61F 9/04* (2013.01); *G06F 3/012* (2013.01); *G06F 3/1454* (2013.01);
(Continued)

(58) Field of Classification Search
CPC .. G06F 21/10; G06F 3/011; G06F 2221/0713; G06F 3/1454; G06F 9/6201;
(Continued)

(56) References Cited

U.S. PATENT DOCUMENTS 6,091,546 A    7/2000 Spitzer
6,452,572 B1    9/2002 Fan et al.
(Continued)

FOREIGN PATENT DOCUMENTS

CN    201054051 Y    4/2008
CN    101258436 A    9/2008
(Continued)

OTHER PUBLICATIONS

International Search Report and Written Opinion dated Feb. 6, 2020, for International Application No. PCT/US2019/056473, 17 pages.
(Continued)

*Primary Examiner* — Jin Cheng Wang
(74) *Attorney, Agent, or Firm* — Frost Brown Todd LLP

(57) ABSTRACT

Service for a machine such as a laboratory instrument can be facilitated by capture of images showing the field of view of a user of the machine, and modification of those images to remove confidential information. Modified images can then be provided to service technicians so that the service technicians can have visual information that would allow them to more effectively communicate and interact with the machines' users.

19 Claims, 7 Drawing Sheets

Related U.S. Application Data

(60) Provisional application No. 62/758,147, filed on Nov. 9, 2018.

(51) Int. Cl.
| | |
|---|---|
| *G06F 3/14* | (2006.01) |
| *G06F 18/22* | (2023.01) |
| *G06F 21/60* | (2013.01) |
| *G06V 20/10* | (2022.01) |
| *H04B 1/3827* | (2015.01) |
| *H04N 5/272* | (2006.01) |
| *H04N 23/56* | (2023.01) |
| *H04N 23/61* | (2023.01) |

(52) U.S. Cl.
CPC ............ *G06F 18/22* (2023.01); *G06V 20/10* (2022.01); *H04N 5/272* (2013.01); *H04N 23/56* (2023.01); *H04N 23/61* (2023.01); *G06F 21/602* (2013.01); *G06V 2201/02* (2022.01); *H04B 1/3827* (2013.01)

(58) Field of Classification Search
CPC .......... G06F 2221/2149; G06F 3/0163; G06F 1/163; G09G 5/377; G09G 2358/00; G09G 2340/12; G02B 27/017; G06T 19/006; G06T 7/194; G08B 13/19686
See application file for complete search history.

(56) References Cited

U.S. PATENT DOCUMENTS

| | | | |
|---|---|---|---|
| 7,230,582 B1 | 6/2007 | Dove et al. |
| 7,372,451 B2 | 5/2008 | Dempski et al. |
| 7,447,330 B2 | 11/2008 | Yamasaki |
| 7,511,838 B2 | 3/2009 | Hunter |
| 7,714,895 B2 | 5/2010 | Pretlove et al. |
| 7,715,037 B2 | 5/2010 | Castellani et al. |
| 8,373,618 B2 | 2/2013 | Friedrich et al. |
| 8,430,507 B2 | 4/2013 | Howell et al. |
| 8,434,863 B2 | 5/2013 | Howell et al. |
| 8,471,783 B2 | 6/2013 | Rhodes |
| 8,531,355 B2 | 9/2013 | Maltz |
| 8,531,394 B2 | 9/2013 | Maltz |
| 8,621,362 B2 | 12/2013 | Castellani et al. |
| 8,681,073 B1 | 3/2014 | Robbins et al. |
| 8,681,256 B2 | 3/2014 | Sako et al. |
| 8,872,941 B2 | 10/2014 | Asukai et al. |
| 8,934,015 B1 | 1/2015 | Chi et al. |
| 8,982,013 B2 | 3/2015 | Sako et al. |
| 9,122,321 B2 | 9/2015 | Perez et al. |
| 9,128,520 B2 | 9/2015 | Geisner et al. |
| 9,132,342 B2 | 9/2015 | Balachandreswaran et al. |
| 9,153,074 B2 | 10/2015 | Zhou et al. |
| 9,160,993 B1 | 10/2015 | Lish et al. |
| 9,213,163 B2 | 12/2015 | Lewis et al. |
| 9,255,813 B2 | 2/2016 | Liu et al. |
| 9,286,711 B2 | 3/2016 | Geisner et al. |
| 9,323,983 B2 | 4/2016 | Monnerat et al. |
| 9,329,689 B2 | 5/2016 | Osterhout et al. |
| 9,330,313 B2 | 5/2016 | Jung et al. |
| 9,342,751 B2 | 5/2016 | Heo et al. |
| 9,470,894 B2 | 10/2016 | Lee et al. |
| 9,493,125 B2 | 11/2016 | Heo |
| 9,547,184 B2 | 1/2017 | Howell et al. |
| 9,667,855 B2 | 5/2017 | Kim et al. |
| 9,686,466 B1 | 6/2017 | Billinghurst et al. |
| 9,690,099 B2 | 6/2017 | Bar-Zeev et al. |
| 9,706,106 B2 | 7/2017 | Kang et al. |
| 9,710,099 B2 | 7/2017 | Rhee et al. |
| 9,729,767 B2 | 8/2017 | Longbotham et al. |
| 9,729,819 B2 | 8/2017 | Im et al. |
| 9,734,402 B2 | 8/2017 | Jang et al. |
| 9,766,463 B2 | 9/2017 | Border et al. |
| 9,787,890 B2 | 10/2017 | Cho et al. |
| 9,841,599 B2 | 12/2017 | Border |
| 9,860,411 B2 | 1/2018 | Ju et al. |
| 9,866,757 B2 | 1/2018 | He et al. |
| 9,874,998 B2 | 1/2018 | Woo et al. |
| 9,892,561 B2 | 2/2018 | Choukroun et al. |
| 9,904,369 B2 | 2/2018 | Lai et al. |
| 10,546,557 B2* | 1/2020 | Jain ...................... G06F 3/1454 |
| 10,593,066 B1* | 3/2020 | Dhua ...................... G06T 7/70 |
| 2007/0052672 A1 | 3/2007 | Ritter et al. |
| 2008/0100570 A1 | 5/2008 | Friedrich et al. |
| 2012/0127284 A1 | 5/2012 | Bar-Zeev et al. |
| 2013/0083011 A1 | 4/2013 | Geisner et al. |
| 2013/0083063 A1 | 4/2013 | Geisner et al. |
| 2013/0278636 A1 | 10/2013 | Ota et al. |
| 2013/0286163 A1 | 10/2013 | Dror et al. |
| 2014/0085183 A1 | 3/2014 | Na |
| 2014/0380446 A1 | 12/2014 | Niu et al. |
| 2015/0062161 A1 | 3/2015 | Kim et al. |
| 2015/0095041 A1 | 4/2015 | Kim |
| 2015/0156803 A1* | 6/2015 | Ballard ................. G06F 3/0485 455/422.1 |
| 2015/0235610 A1 | 8/2015 | Miller et al. |
| 2015/0293345 A1 | 10/2015 | Laxhuber et al. |
| 2015/0309316 A1 | 10/2015 | Osterhout et al. |
| 2015/0362729 A1 | 12/2015 | Jang et al. |
| 2016/0027215 A1* | 1/2016 | Burns ................ G02B 27/0103 345/626 |
| 2016/0034032 A1 | 2/2016 | Jeong |
| 2016/0078449 A1 | 3/2016 | Banerjee |
| 2016/0147492 A1* | 5/2016 | Fugate .................. G06F 3/1423 345/633 |
| 2016/0171780 A1 | 6/2016 | Vardi |
| 2016/0314759 A1 | 10/2016 | Shin et al. |
| 2016/0350975 A1 | 12/2016 | Nakagawa |
| 2017/0061212 A1 | 3/2017 | Tanaka et al. |
| 2017/0064207 A1 | 3/2017 | Kim et al. |
| 2017/0064209 A1 | 3/2017 | Cohen et al. |
| 2017/0069135 A1 | 3/2017 | Komaki et al. |
| 2017/0078755 A1 | 3/2017 | Jang et al. |
| 2017/0097802 A1 | 4/2017 | Jeong |
| 2017/0180646 A1 | 6/2017 | Kim et al. |
| 2017/0206509 A1 | 7/2017 | Beyk et al. |
| 2017/0230641 A1 | 8/2017 | Scavezze et al. |
| 2017/0318226 A1 | 11/2017 | Jung et al. |
| 2017/0337352 A1* | 11/2017 | Williams ................ G06F 21/10 |
| 2017/0351920 A1 | 12/2017 | Tanaka et al. |
| 2017/0364162 A1 | 12/2017 | Fujimaki et al. |
| 2018/0011344 A1 | 1/2018 | Calilung et al. |
| 2018/0082020 A1* | 3/2018 | Rajagopal ............. G16H 10/60 |
| 2018/0107805 A1* | 4/2018 | Anantharaman ....... G06F 21/10 |
| 2018/0157333 A1* | 6/2018 | Ross ...................... G06F 3/013 |
| 2018/0293041 A1* | 10/2018 | Harviainen .......... H04N 13/361 |
| 2019/0088017 A1* | 3/2019 | Sato .......................... G06T 7/70 |
| 2019/0122437 A1* | 4/2019 | Pinti ..................... G06T 19/006 |
| 2019/0197254 A1* | 6/2019 | Salgar .................. G06V 20/52 |
| 2019/0206141 A1* | 7/2019 | Deng .................. G06V 40/172 |
| 2019/0340333 A1* | 11/2019 | Srinivasan ............. G06F 21/84 |
| 2019/0340815 A1* | 11/2019 | Yildiz ..................... G06F 3/011 |
| 2019/0370544 A1* | 12/2019 | Wright, Jr. ......... G02B 27/0101 |
| 2020/0013373 A1 | 1/2020 | Sugaya |
| 2020/0082600 A1* | 3/2020 | Jones ................... G06T 19/006 |
| 2020/0097065 A1* | 3/2020 | Iyer ........................ G06F 3/017 |
| 2020/0322506 A1 | 10/2020 | Ikegame et al. |
| 2020/0404122 A1* | 12/2020 | Kim ..................... H04N 1/0044 |
| 2021/0200886 A1* | 7/2021 | Ramamurthy ........ G06F 21/629 |

FOREIGN PATENT DOCUMENTS

| | | |
|---|---|---|
| CN | 102866506 A | 1/2013 |
| CN | 101819334 B | 4/2013 |
| CN | 203399222 U | 1/2014 |
| CN | 102348068 B | 11/2014 |
| CN | 102591016 B | 12/2014 |
| CN | 104182050 A | 12/2014 |
| CN | 204009265 U | 12/2014 |
| CN | 104570399 A | 4/2015 |
| CN | 204390168 U | 6/2015 |
| CN | 104950448 A | 9/2015 |
| CN | 204636276 U | 9/2015 |

(56) References Cited

FOREIGN PATENT DOCUMENTS

| | | |
|---|---|---|
| CN | 104090385 B | 11/2015 |
| CN | 105158900 A | 12/2015 |
| CN | 105158927 A | 12/2015 |
| CN | 105158931 A | 12/2015 |
| CN | 105182536 A | 12/2015 |
| CN | 105184276 A | 12/2015 |
| CN | 105204643 A | 12/2015 |
| CN | 105205471 A | 12/2015 |
| CN | 105223706 A | 1/2016 |
| CN | 105224923 A | 1/2016 |
| CN | 105242401 A | 1/2016 |
| CN | 105259657 A | 1/2016 |
| CN | 105353508 A | 2/2016 |
| CN | 105353509 A | 2/2016 |
| CN | 105353510 A | 2/2016 |
| CN | 105355196 A | 2/2016 |
| CN | 105357421 A | 2/2016 |
| CN | 103186922 B | 8/2016 |
| CN | 205427327 U | 8/2016 |
| CN | 106028000 A | 10/2016 |
| CN | 205847478 U | 12/2016 |
| CN | 106291985 A | 1/2017 |
| CN | 205864618 U | 1/2017 |
| CN | 103856590 B | 5/2017 |
| CN | 103529929 B | 6/2017 |
| CN | 104221077 B | 7/2017 |
| CN | 104423038 B | 7/2017 |
| CN | 107272224 A | 10/2017 |
| CN | 107340853 A | 10/2017 |
| CN | 206584114 U | 10/2017 |
| CN | 107680069 A | 2/2018 |
| EP | 2712213 A1 | 3/2014 |
| EP | 2741172 A3 | 8/2015 |
| EP | 3352456 A1 | 7/2018 |
| GB | 2533553 A | 6/2016 |
| JP | 2000-349999 A | 12/2000 |
| JP | 2002-369054 A | 12/2002 |
| JP | 2004-363987 A | 12/2004 |
| JP | 2007-173992 A | 7/2007 |
| JP | 4051702 B2 | 2/2008 |
| JP | 2008-146109 A | 6/2008 |
| JP | 2009-147647 A | 7/2009 |
| JP | 2012-168642 A | 9/2012 |
| JP | 2013-236213 A | 11/2013 |
| JP | 2014-212473 A | 11/2014 |
| JP | 2015-115723 A | 6/2015 |
| JP | 2015-228009 A | 12/2015 |
| JP | 2016-045724 A | 4/2016 |
| JP | 2016-146044 A | 8/2016 |
| JP | 5965410 B2 | 8/2016 |
| JP | 2016-218905 A | 12/2016 |
| JP | 2016-224086 A | 12/2016 |
| JP | 2017-010119 A | 1/2017 |
| JP | 2017-049762 A | 3/2017 |
| JP | 2017-142857 A | 8/2017 |
| JP | 2017-195552 A | 10/2017 |
| JP | 2017-211766 A | 11/2017 |
| JP | 2018-011242 A | 1/2018 |
| JP | 2018-116572 A | 7/2018 |
| JP | 2018-156293 A | 10/2018 |
| JP | 2018-179222 A | 11/2018 |
| JP | JP WO 2018-179222 | 4/2019 |
| JP | 2018-037951 A | 9/2019 |
| KR | 10-0653303 B1 | 5/2006 |
| KR | 2014-0072651 A | 6/2014 |
| KR | 2014-0146889 A | 12/2014 |
| KR | 2015-0001912 A | 1/2015 |
| KR | 2015-0130767 A | 11/2015 |
| KR | 2016-0066068 A | 6/2016 |
| KR | 2017-0087247 A | 7/2017 |
| WO | WO 2001/095061 A2 | 12/2001 |
| WO | WO 2013/077895 A1 | 5/2013 |
| WO | WO 2014/144918 A3 | 1/2015 |
| WO | WO 2015/032014 A1 | 3/2015 |
| WO | WO 2016/010328 A1 | 1/2016 |
| WO | WO 2016/069588 A1 | 5/2016 |
| WO | WO 2018/014534 A1 | 1/2018 |

OTHER PUBLICATIONS

International Search Report and Written Opinion dated Jun. 12, 2020, for International Application No. PCT/US2020/028652, 8 pages.

U.S. Appl. No. 17/289,345, entitled "Securing Data of Objects in a Laboratory Environment," filed Apr. 28, 2021.

Japanese Patent Application No. 2021-524368, Office Action dated Oct. 19, 2023, 16 pages.

\* cited by examiner

101 Safety Glasses
102 LED indicator
103 Camera
104 Gesture sensor
105 Bone speaker
106 Battery & USB charger
107 Microphone

SERVICE GLASSES WITH SELECTIVE
DATA PROVISION

RELATED APPLICATIONS

This is a continuation of International Patent Application No. PCT/US19/056473, entitled "Service Glasses with Selective Data Provision," filed Oct. 16, 2019, which claims benefit of, provisional patent application 62/758,147, titled "Service Glasses with Selective Data Provision," filed in the United States Patent Office on Nov. 9, 2018, the disclosures of which are hereby incorporated by reference in their entirety.

TECHNICAL FIELD

The technology disclosed herein may be applicable to laboratory instruments.

BACKGROUND

From time to time, laboratory instruments, such as instruments used to analyze blood samples from patients, may experience issues that are beyond the capabilities of the individuals at the location of the instrument to solve. To address this, external service personnel having greater expertise may be involved to provide either onsite or remote support. However, the involvement of these external service personnel may be complicated by the fact that the laboratory instruments may generate or display highly sensitive data that should not be exposed beyond a highly select population that may not include the service personnel. Accordingly, there is a need for technology that can allow external service personnel to provide assistance with resolving issues related to laboratory equipment while preventing those service personnel from being exposed to highly sensitive data.

SUMMARY

Embodiments disclosed herein may be used to implement methods and machines for providing service to laboratory instruments without inappropriately exposing sensitive information. For example, embodiments disclosed herein may be used to perform a method which comprises capturing an image of a field of view of a wearer of a head mounted camera and generating a modified image by performing a set of steps. Such steps may include identifying one or more display screens in the wearer's field of view. Such steps may also include, for each of the one or more display screens, determining whether an interface is displayed on that display screen that matches an item from a predefined interface library. Such steps may also include, for each displayed interface with a matching item from the predefined interface library, either overlaying an image corresponding to that interface from the predefined interface library or masking confidential information in that interface based on information from the predefined interface library indicating one or more confidential information locations in that interface. Such a method may also include presenting the modified image, and such presentation may comprise transmitting the modified image to a remote service technician or displaying the modified image on a display of an augmented reality headpiece on which the head mounted camera is integrated.

Other embodiments are also possible. For example, the disclosed technology may be used to implement a system comprising a head mounted camera and a processor. In such a system, the processor may be configured with a set of computer instructions operable to, when executed, determine whether images captured by the head mounted camera should be made available for non-immediate viewing. In some embodiments, such a determination may be made after the head mounted camera has been activated. Additionally, in some embodiments of this type of system, the computer instructions configuring the processor may make operable making an image captured by the head mounted camera available for non-immediate viewing if and only if a determination was made that images captured by the head mounted camera should be made available for non-immediate viewing prior to that image being captured, and no determination was made that images captured by the head mounted camera should be made available for non-immediate viewing more recently than the most recent determination that images captured by the head mounted camera should be made available for non-immediate viewing.

Further information on how the disclosed technology could potentially be implemented is set forth herein, and variations on the examples will be immediately apparent to and could be practiced without undue experimentation by those of ordinary skill in the art based on the material which is set forth in this document. Accordingly, exemplary methods and machines described in this summary should be understood as being illustrative only, and should not be treated as limiting the scope of protection provided by this or any related document.

DETAILED DESCRIPTION

Figure 1:
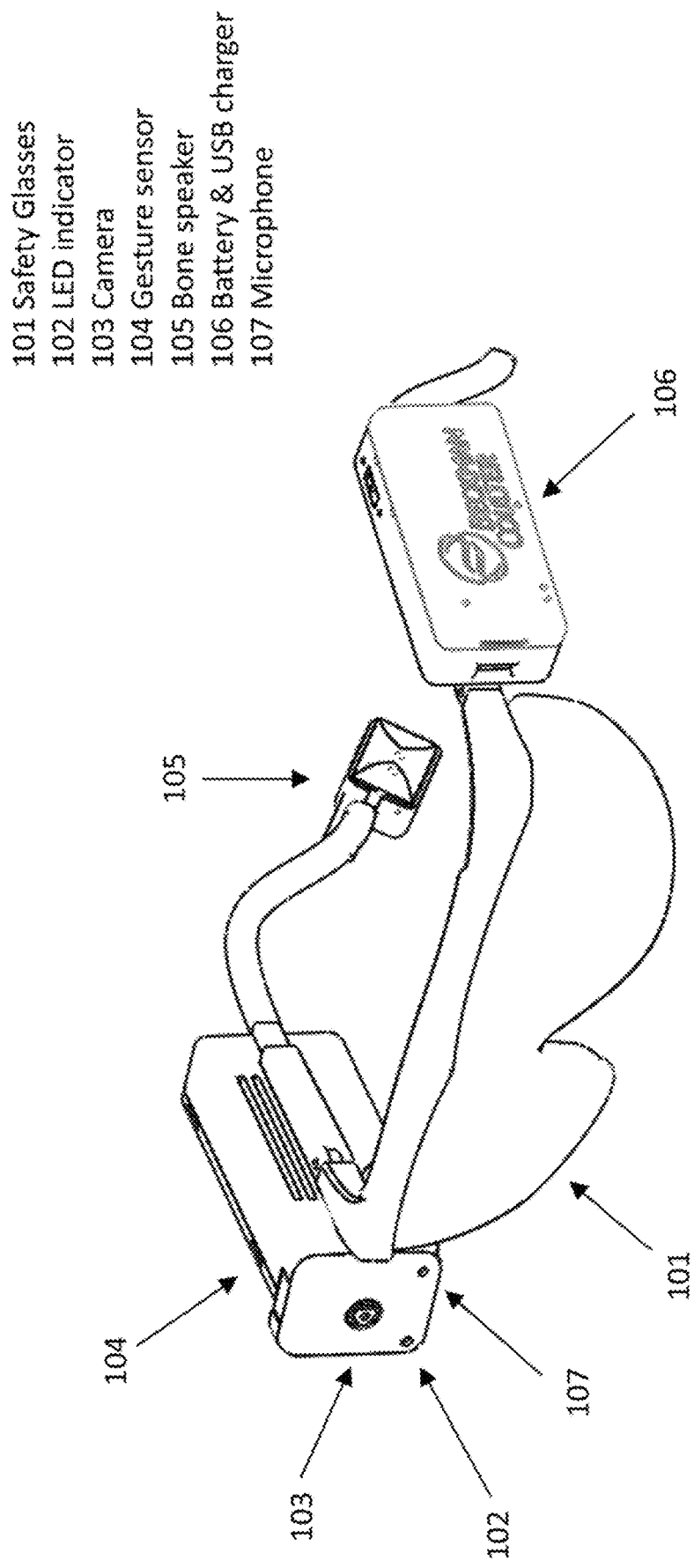
FIG. 1 illustrates a pair of instrumented safety glasses which may be used in some embodiments.

The technology disclosed herein can be used to address problems related to servicing laboratory equipment while preventing exposure of confidential information.

According to a first aspect, some embodiments may include a method comprising capturing an image of a field of view of a wearer of a head mounted camera, automatically generating a modified image in real time, and presenting the modified image. In such methods, automatically generating the modified image may comprise steps such as identifying one or more portions of the image of the field of view of the wearer of the head mounted camera to be masked and masking each of the one or more identified portions. Additionally, in methods such as referred to above, presenting the modified image may comprise transmitting the modified image to a remote service technician, displaying the modified image on a display of an augmented reality headpiece wherein the head mounted camera is integrated with the augmented reality headpiece, or displaying the modified image on a display of a laboratory instrument.

In some embodiments such as described in the context of the first aspect, the step of identifying one or more portions of the image of the field of view of the wearer of the head mounted camera to be masked may comprise a set of steps. Such steps may include identifying one or more display screens in the wearer's field of view. Such steps may also comprise, for each of the one or more display screens, determining whether an interface is displayed on that display screen that matches an item from a predefined interface library. Such steps may also include, for each displayed interface with a matching item from the predefined interface library, identifying one or more portions of that interface as portions of the image to be masked based on information from the matching item from the predefined interface library. In some such embodiments, masking each of the one or more identified portions may comprise, for each of the one or more display screens having a matching item from the predefined interface library, overlaying an image corresponding to that interface from the predefined interface library.

In some embodiments such as described in the context of the first aspect, identifying one or more portions of the image of the field of view of the wearer of the head mounted camera to be masked may comprise determining a focal distance of the head mounted camera and identifying each portion of the image of the field of view of the wearer of the head mounted camera that is farther from the head mounted camera than the identified focal distance as a portion of the image of the field of view of the wearer of the head mounted camera to be masked.

In some embodiments such as described in the context of the first aspect, the method might comprise, prior to capturing the image of the field of view of the wearer of the head mounted camera, providing one or more notation media exemplary images. Further, in such an embodiment, identifying one or more portions of the image of the field of view of the wearer of the head mounted camera to be masked may comprise identifying one or more notation media in the wearer's field of view based on information from the notation media exemplar images, and identifying each notation media in the wearer's field of view as a portion of the image of the field of the wearer to be masked. Similarly, in some such embodiments, the information from the notation media exemplar images may comprise one or more notation media exemplar colors.

In some embodiments such as described in the context of the first aspect, the method may comprise, prior to capturing the image of the field of view of the wearer of the head mounted camera, specifying an imagable area of a laboratory. In such an embodiment, the method may also comprise, after capturing the image of the field of view of the wearer of the head mounted camera, determining (which determination may be based on one or more wireless transceivers located at a border of the imagable area, or based on distance from a wireless transceiver located inside the imagable area) whether the head mounted camera is located in the imagable area of the laboratory. Additionally, in some embodiments where presenting the modified image comprises transmitting the modified image to a remote service technician, based on a determination that the head mounted camera is not located in the imagable area of the laboratory, the method may include automatically deactivating transmission functionality of the head mounted camera. In some such embodiments, deactivating transmission functionality of the head mounted camera may be done by deactivating the head mounted camera.

In some embodiments such as described in the context of the first aspect, presenting the modified image may comprise transmitting the modified image to a remote service technician using an internet connection. Additionally, in some such embodiments, the method may comprise, simultaneously with transmitting the modified image to a remote service technician, displaying the image of the field of view of the wearer of the head mounted camera on a display of an augmented reality headpiece. In some such embodiments, the head mounted camera may be integrated with the augmented reality headpiece. Additionally, in some embodiments the head mounted camera may be comprised by a pair of instrumented safety glasses.

In some embodiments such as described in the context of the first aspect, the image of the field of view of the wearer of the head mounted camera may be captured as part of a video stream. In some such embodiments, the method may comprise transmitting the modified image to the remote service technician, and that transmission may be performed by transmitting a version of the video stream that includes the modified image rather than the captured image.

In some embodiments such as described in the context of the first aspect, the automatic generation of the modified image may be completed no more than ten seconds after capturing the image of the field of view of the wearer of the head mounted camera. In some such embodiments, the delay between capturing the field of view of the wearer of the head mounted camera and completion of generation of the modified image may be no more than 5 seconds, no more than 1 second, no more than 0.5 second, or no more than 0.1 second. Additionally, in some embodiments such as described in the context of the first aspect, the image of the field of view of the wearer of the head mounted camera may include confidential information outside of the one or more portions identified as portions to be masked.

According to a second aspect, some embodiments may include a system comprising a head mounted camera and a processor. In such embodiments, the processor may be configured with a set of computer instructions operable to, when executed, perform a variety of steps. Such steps may include, after the head mounted camera has been activated, determining whether images captured by the head mounted camera should be made available for non-immediate viewing and making an image captured by the head mounted camera available for non-immediate viewing if and only if various conditions are satisfied. Such conditions may include, in some embodiments, a determination is made that that image should be made available for non-immediate viewing, and/or both of the following statements are true: (1) a determination was made that images captured by the head mounted camera should be made available for non-immediate viewing prior to that image being capture and (2) no determination was made that images captured by the head mounted camera should not be made available for non-immediate viewing more recently than the most recent determination that images captured by the head mounted camera should be made available for non-immediate viewing.

In some embodiments such as described in the context of the second aspect, the computer instructions may be operable to, when executed, determine whether images captured by the head mounted camera should be made available for non-immediate viewing by performing a set of steps comprising determining if the head mounted camera is located within a predefined area. Such a set of steps may also include, based on a determination that the head mounted camera is not located within the predefined area, determining that images captured by the head mounted camera should not be made available for non-immediate viewing. In some such embodiments, the system may comprise a wireless transceiver located inside the predefined area, and the determination that the head mounted camera is not located within the predefined area is based on a distance between the head mounted camera and the wireless transceiver. In some other such embodiments, the system may comprise one or more wireless transceivers located at a border of the predefined area, and the determination that the head mounted camera is not located within the predefined area is based on detection of the head mounted camera crossing the border of the predefined area.

In some embodiments such as described in the context of the second aspect, the system may comprise a laboratory instrument, and the computer instructions may be operable to, when executed, determine whether images captured by the head mounted camera should be made available for non-immediate viewing by performing a set of steps. Such steps may include determining an orientation of the head mounted camera relative to the laboratory instrument, and, based on a determination that the orientation of the head mounted camera is offset from the laboratory instrument by 90 degrees or more, determining that images captured by the head mounted camera should not be made available for non-immediate viewing.

In some embodiments such as described in the context of the second aspect, the computer instructions may be operable to, when executed, determine whether images captured by the head mounted camera should be made available for non-immediate viewing by performing a set of steps comprising, based on a determination that elapsed time since a most recent occurrence of an authorization action is greater than a threshold duration, determining that images captured by the head mounted camera should not be made available for non-immediate viewing.

In some embodiments such as described in the context of the second aspect, the system may comprise a laboratory instrument configured to wirelessly communicate with the head mounted camera and/or to encrypt images captured by the head mounted camera.

In some embodiments such as described in the context of the second aspect, the head mounted camera may comprise an exterior light source. In such an embodiment, the head mounted camera may be configured to activate the exterior light source when the head mounted camera is activated and when a determination is made that images captured by the head mounted camera should be made available for non-immediate viewing. Similarly, in some such embodiments, the head mounted camera may be configured to deactivate the exterior light source when the head mounted camera is deactivated and when a determination is made that images captured by the head mounted camera should not be made available for non-immediate viewing.

In a third aspect, some embodiments may include a machine comprising a head mounted camera and a means for generating modified images which lack confidential information included in images captured by the head mounted camera.

Various other aspects and embodiments are also possible and could be implemented by those of ordinary skill in the art without undue experimentation based on the disclosure set forth herein. Accordingly, the above discussion and the features from the examples set forth in this description should not be treated as implying limitations on the protection provided by this document or by any other document which claims the benefit of this disclosure.

Figure 4:
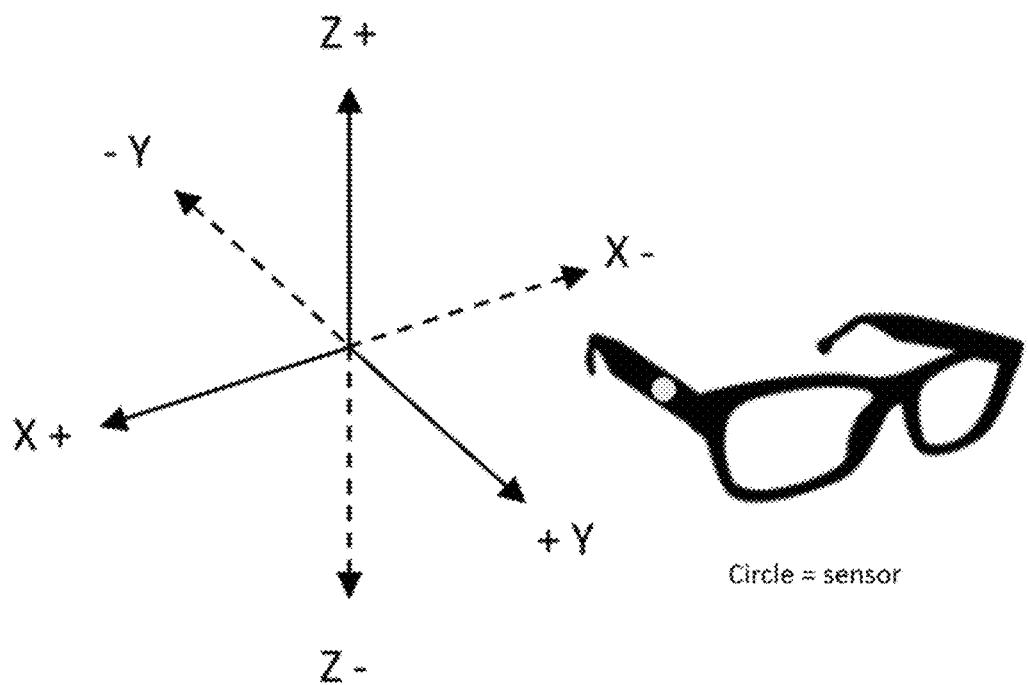
FIG. 4 illustrates exemplary gestures that may be recognized and associated with commands by a gesture sensor in some embodiments.

Turning now to FIG. 1, that figure illustrates a pair of instrumented safety glasses 101 which may be used in some embodiments. As will be appreciated by those of skill in the art, operators of laboratory instruments can be expected to (and generally are required to) wear safety glasses at all times when operating the instruments, and so such safety glasses may provide a convenient platform for technology that would allow the operator to obtain assistance from a remote service technician without exposing confidential information to such technician. As shown in FIG. 1, a pair of instrumented safety glasses 101 may include a camera 103, a LED indicator 102, a gesture sensor 104, a speaker 105, a power supply 106, and a microphone 107. In some embodiments, a camera 103 on a pair of instrumented glasses 101 may be configured to (when activated) capture images in a field of view of the individual wearing the glasses 101. The LED indicator 102 may be configured to automatically illuminate when the camera 103 was either recording or transmitting, so that others in the vicinity would not be recorded without their knowledge. The gesture sensor 104 could be implemented using a processor and software programmed to recognize a set of predefined gestures to allow for hands free operation of the instrumented glasses 101. Examples of such gestures are shown in FIG. 4, though it should be understood that other gestures and associated actions may be included in some embodiments (e.g., treating clockwise/counterclockwise circles by the user as commands to turn a video feed on/off), and so the examples illustrated in FIG. 4 should not be treated as implying limitations on the types of gestures or associated commands that could be supported by embodiments of the disclosed technology. The speaker 105, which would preferably be implemented as a bone conduction speaker, could allow the individual wearing the instrumented glasses 101 to receive auditory information (e.g., instructions or questions from a remote service technician) without disturbing the other individuals in his or her vicinity. The power source 106 could be implemented using a USB chargeable and/or replaceable battery that could provide power to the other components of the instrumented glasses 101 (e.g., camera 103, LED indicator 102, etc.). The microphone 107 could be an electret or other type of microphone, could be disposed at various locations, such as on the stem of a pair of instrumented glasses 101 or as a headset microphone on an arm locating it proximate to the user's mouth (not shown in FIG. 1), and could be used for various purposes, such as capturing speech input during a conversation between the wearer of the instrumented glasses 101 and a remote service technician.

It should be understood that, while FIG. 1 illustrates various components that may be included in a pair of instrumented safety glasses 101, other or different components may be included in some embodiments, and that the instrumented safety glasses of FIG. 1 should be seen as being illustrative only, rather than being treated as limiting. For example, a pair of instrumented glasses 101 will preferably include a transceiver, or a transmitter and receiver pair configured to allow data communication with external devices or entities, such as remote service technicians. Such a transceiver may allow direct communication with remote technicians (e.g., in the case of a cellular transceiver) or may instead facilitate indirect communication, (e.g., in the case of a Bluetooth transceiver or WiFi transceiver such as could establish a connection through a separate cellular phone or computer). Further, in some embodiments, a pair of instrumented glasses 101 may provide the capability to present augmented reality information, such as through a separate translucent screen positioned in the user's field of view, or through integration of optical display elements into the lenses of the instrumented glasses 101 themselves. Further variations, such as alternative placement of components (e.g., placement of the camera 103 on the bridge of the glasses, rather than on a stem) or omission of components (e.g., omission of the gesture sensor 104) are also possible and will be immediately apparent to those of ordinary skill in the art in light of the explicit disclosure set forth herein.

Of course, it should be understood that, like the configurations of components described above, instrumented safety glasses 101 such as shown in FIG. 1 are intended to be illustrative only, and should not be seen as limiting on the types of physical devices which could be used in various embodiments of the disclosed technology. For example, some embodiments could utilize software such as software created using the ARCore augmented reality framework to allow a smartphone, potentially in combination with headgear that would allow the smartphone display to occupy the user's field of view, to be used instead of instrumented glasses 101 such as shown in FIG. 1. Alternatively, commercially available augmented reality devices, such as the Rift from Oculus VR, LLC may be used in some embodiments. As yet another alternative, while preferred embodiments of the disclosed technology will be implemented in a manner that allows hands free interaction by a user, some embodiments may utilize handheld devices (e.g., tablets, smartphones without headsets) to provide functionality from various aspects of the disclosed technology. Accordingly, the instrumented safety glasses 101 of FIG. 1 should be understood as being illustrative only, and should not be treated as limiting.

Figure 2:
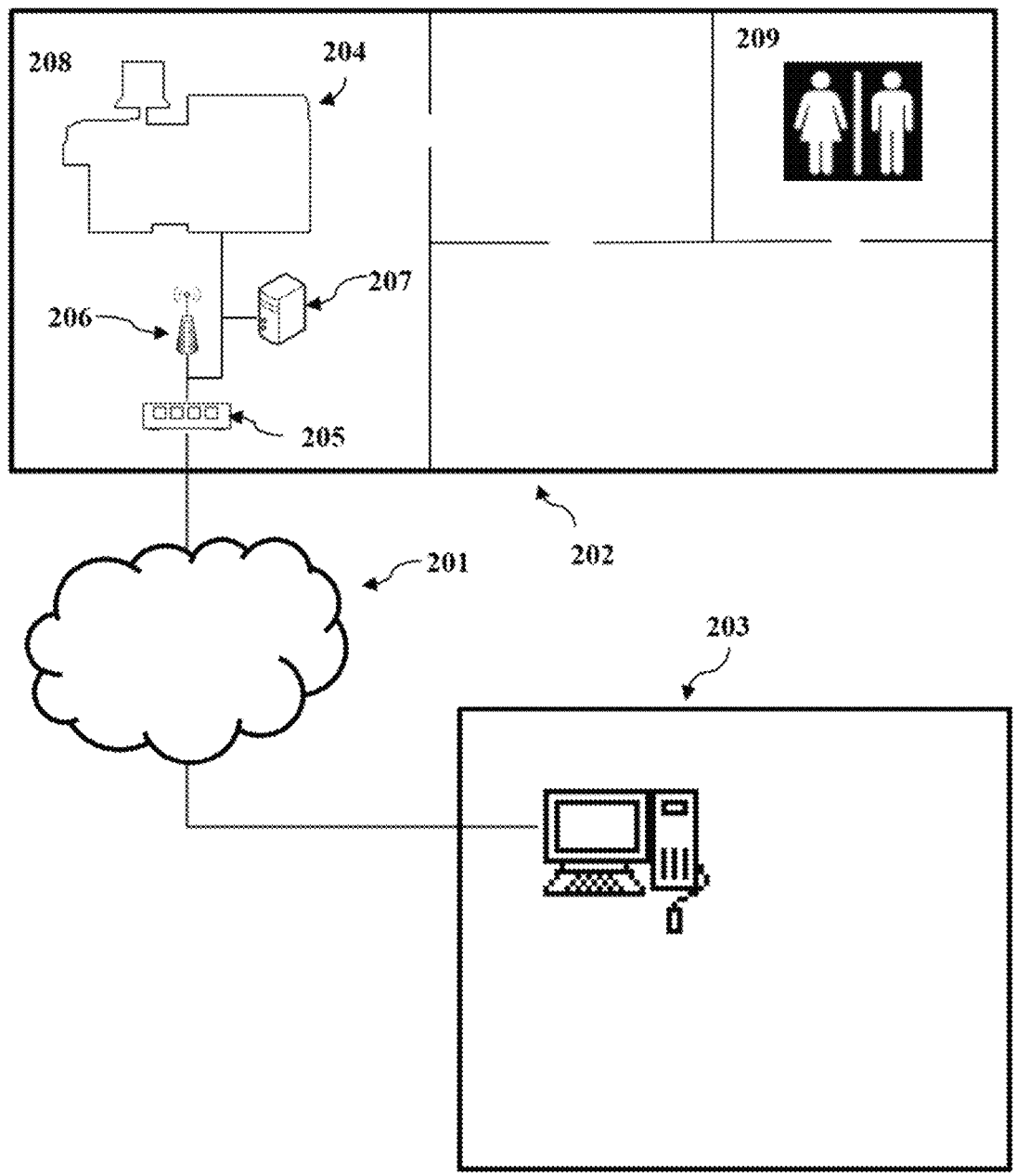
FIG. 2 illustrates an exemplary environment in which aspects of the disclosed technology may be deployed.

Turning now to FIG. 2, that figure illustrates an exemplary environment in which aspects of the disclosed technology may be deployed. In that environment, a network 201 is used to establish a connection between a laboratory 202 and a remote support provider 203. In this type of environment, it is possible that a laboratory instrument 204 may have a communication path which indirectly connects with the remote support provider 203 through a dedicated hardware interface 205 that could provide functionality such as buffering, encryption and/or establishing a VPN connection between the laboratory 202 and the support provider 203. Additionally, in some embodiments deployed in an environment such as shown in FIG. 2, a hardware network interface 205 may also be connected to a wireless access point 206 that could be used to communicate with instrumented glasses 101 such as shown in FIG. 1 and/or a local computer 207 that could be used in some embodiments to support such instrumented glasses' functionality.

It should be understood that, just as it is possible that some embodiments may use devices that vary from the instrumented glasses 101 shown in FIG. 1, it is possible that various embodiments may use different devices and/or combinations of devices than shown in FIG. 2. For example, in some embodiments rather than including a separate hardware interface 205, a laboratory instrument 204 and/or a local computer 207 may be directly connected to a remote support provider 203, such as by being configured with a virtual machine that provides functionality similar to the separate hardware interface 205 of FIG. 2. Similarly, in some embodiments a local computer 207 separate from the laboratory instrument 204 may be omitted, and the functionality of the disclosed technology may instead be supported by the processing capabilities of a set of instrumented glasses (e.g., using the same processor and software described previously for the gesture sensor 104) and/or by the laboratory instrument 204 itself. Additionally, in some embodiments functionality that could be provided by a local computer 207 and/or a set of instrumented glasses may instead be supported by the remote support provider 203 or other remote system (e.g., a separate server remote from both the laboratory instrument 204 and the remote support provider 203). For example, in some embodiments, it may be possible that an image captured by a camera on a pair of instrumented glasses at the laboratory instrument may be transmitted in encrypted form to a remote support provider (or separate remote server) and be processed at that location (e.g., by removing confidential information, as described in more detail herein) rather than by a computer at or proximate to the laboratory instrument itself. Accordingly, the environment of FIG. 2 should be understood as being illustrative only, and should not be treated as limiting.

Figure 3:
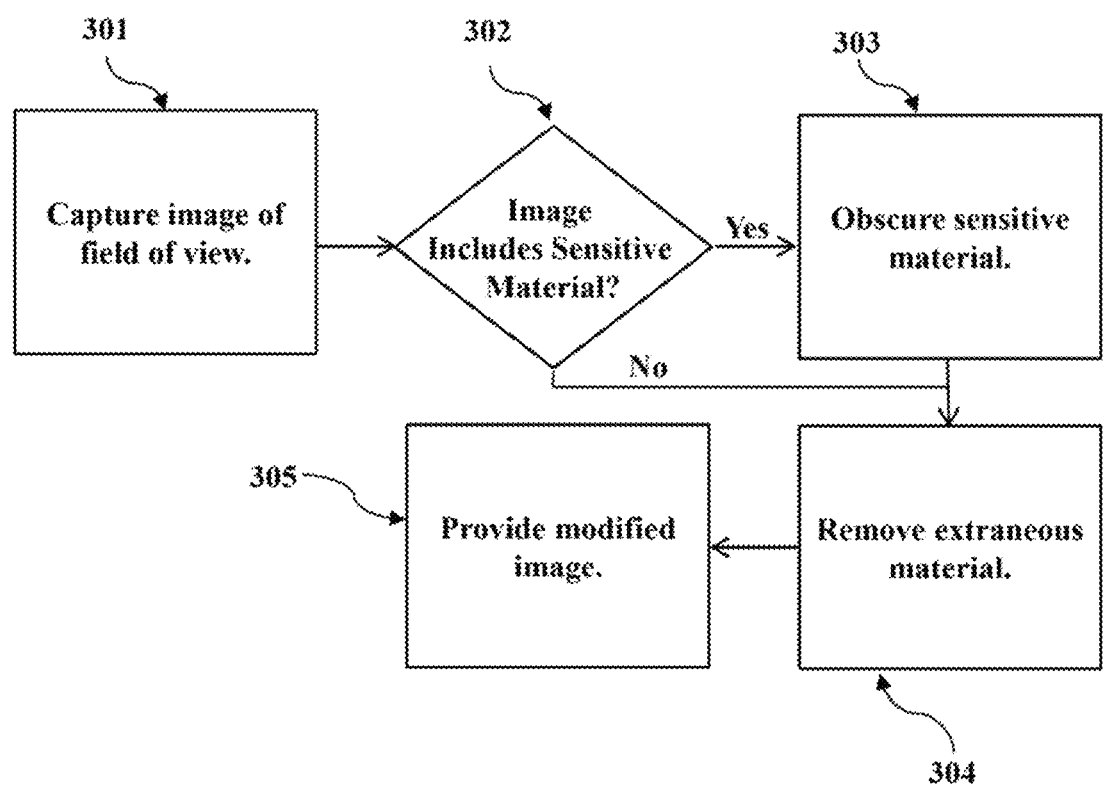
FIG. 3 illustrates a process that may be used in some embodiments to allow an operator of a laboratory instrument to provide useful service information to a remote technician without exposing that remote technician to confidential information that might be displayed by the laboratory instrument.

Turning now to FIG. 3, that figure illustrates a process that may be used in some embodiments to allow an operator of a laboratory instrument to provide useful service information to a remote technician without inadvertently exposing that remote technician to confidential information. Initially, in the process of FIG. 3, an image of the user's field of view (e.g., in an embodiment where the user is wearing a pair of instrumented safety glasses 101, it should be understood that this field of view could be the field of view of the camera 103, rather than necessarily being the same as the actual field of view of the user) is captured 301. Next, a determination 302 can be made of whether the image includes sensitive information that should not be provided to a remote technician. This can be done, for example, by analyzing the image to identify portions that appear to be sticky notes such as could have confidential information written on them, by analyzing the image to identify portions that appear to be barcodes, by analyzing the image to identify screens or other interfaces that may display confidential information, and/or by analyzing the image to identify human faces that might be in the user's field of view but would be immaterial to his or her support requirements. If such information is identified as being present, it could then be obscured 303 in the captured image (e.g., human faces, computer displays, barcodes and/or paper notes may be blurred). Also, as shown in FIG. 3, some embodiments may also include an additional step of automatically removing 304 extraneous material from the image of the user's field of view. This could be done, for example, by discriminating between objects in terms of depth and blurring out all objects except those that were less than a threshold distance from the user, or by identifying the camera's focal distance and blurring out all objects farther from the user than that distance. Finally, once the identified sensitive information had been obscured 303 and the extraneous material had been removed 304, the modified image could be provided 305 to the remote technician so that he or she would be able to use information about what the user was seeing to provide support.

As with the glasses 101 and environment of FIGS. 1 and 2, the process of FIG. 3 should be understood as being illustrative only, and variations on, or departures from, that process may be included in some embodiments. To illustrate, consider application of techniques such as described above in the context of FIG. 3 to the processing of video streams as opposed to individual images. In some embodiments where images are captured in the form of video streams, a process such as shown in FIG. 3 might be applied to each frame on a frame-by-frame basis in order to generate a modified video stream in which confidential information has been removed. However, in other embodiments (e.g., in order to minimize the processing burden of generating modified images) processing such as shown in FIG. 3 may be performed for fewer than all images in a video stream. For example, in some embodiments, every fifth image may be processed to identify portions of the image that should be obscured, and then the obscuring may be carried forward for and applied to the next four images rather than independently determining portions of an image to be masked for each image in the stream. Similarly, in some cases where a video stream is encoded in a form that uses keyframes and deltas, processing such as shown in FIG. 3 may be applied only to keyframes rather than to images in the stream that are represented as deltas between frames.

Other types of variations in addition (or alternative) to optimization for video processing are also possible. For example, in some embodiments, an additional step might be included of determining whether an image should be provided for non-immediate viewing (i.e., making the image viewable other than locally in real time, such as by sending it to a remote service technician, or by saving it for later review) at all and conditioning the performance of steps such as shown in FIG. 3 on the result of that determination. For instance, in some embodiments a user could be allowed (or required) to define an acceptable imaging area, such as the room 208 housing the instrument 204, and the provision 305 of images (and potentially other steps, such as the depicted image analysis and modification) could be conditioned on whether the images were captured in the acceptable imaging area. In this manner, if the image capture equipment were inadvertently removed from the acceptable imaging area (e.g., if someone wearing instrumented glasses went to a restroom 209 without turning them off) it could be automatically deactivated (either completely, or through deactivation only of functionality that would allow for non-immediate viewing, such as by automatic cessation of image transmission) so as to avoid inadvertently providing information that should not be communicated. To support this type of functionality, in some embodiments an acceptable viewing area's entrances and exits could be outfitted with beacons that could detect transit of the image capture equipment and deactivate (and, in some embodiments, reactivate) it (or aspects of its functionality) as appropriate.

Alternatively, in some embodiments image capture equipment (and/or various functionality of that equipment, such as image transmission or storage functionality) might be configured to only remain active as long as it was within a predetermined radius (which, preferably, would be configurable by a user) or was oriented within a set tolerance (e.g., within 90 degrees) of a set point in an imaging area, such as an access point 206 or a transceiver incorporated into the relevant piece of equipment 204. As another alternative, in some embodiments image capture equipment could be equipped with navigation measurement equipment such as one or more accelerometers and/or GPS receiver and could use that equipment to determine whether its current position in a building was within an acceptable imaging area. Non-location-based approaches to automatically activating/deactivating image capture, processing and/or provision functionality could also (or alternatively) be included in some embodiments. For example, in some embodiments, software controlling operation of a pair of instrumented safety glasses could be configured to automatically check captured images for a prespecified symbol and deactivate some or all of the functionality of those glasses (e.g., by ceasing transmission of images to a remote technician) unless the symbol was recognized. In such an embodiment, the relevant symbol would preferably be affixed to or displayed on a laboratory instrument that may need service, so that if the instrumented glasses' wearer did something unrelated to the machine after service was finished but without turning off the glasses, the glasses could automatically stop capturing images (or performing other tasks) based on the fact that the user was no longer looking at the machine.

As another example of a type of variation that could be present in some embodiments, in some cases a method such as shown in FIG. 3 could be supplemented by various advance configuration/setup steps that would allow for more effective identification and screening of sensitive information. Some examples of this, such as user configuration of acceptable imaging areas (in embodiments where that functionality is supported) have already been noted. However, this should not be seen as an exhaustive description of all types of advance configuration that may be permitted/required in various embodiments. For example, in some embodiments where periodic recognition of a particular symbols is necessary to maintain (full) activity for a set of instrumented glasses, the symbol and/or the frequency (e.g., X minutes) with which the symbol was checked for could be configurable by a user. As another example, in some embodiments, to support functionality of allowing for identification and blurring of sticky notes or other notation media that may include confidential information, there may be a setup process in which a set of images of and/or including sticky notes are captured and used as a training corpus so that, when an image is captured, any sticky notes in that image can be effectively identified (e.g., based on shape and color) and blurred or otherwise screened. Similarly, in some embodiments, a user may perform advance configuration by capturing objects that are both likely to be captured and that would be relevant to remote service personnel (e.g., a laboratory instrument itself) and software controlling operation of a pair of instrumented glasses could then use that information to recognize the relevant objects in captured images and automatically treat everything else as irrelevant (e.g., by blurring or filtering it out of an image that would be provided to a remote technician).

Figure 5:
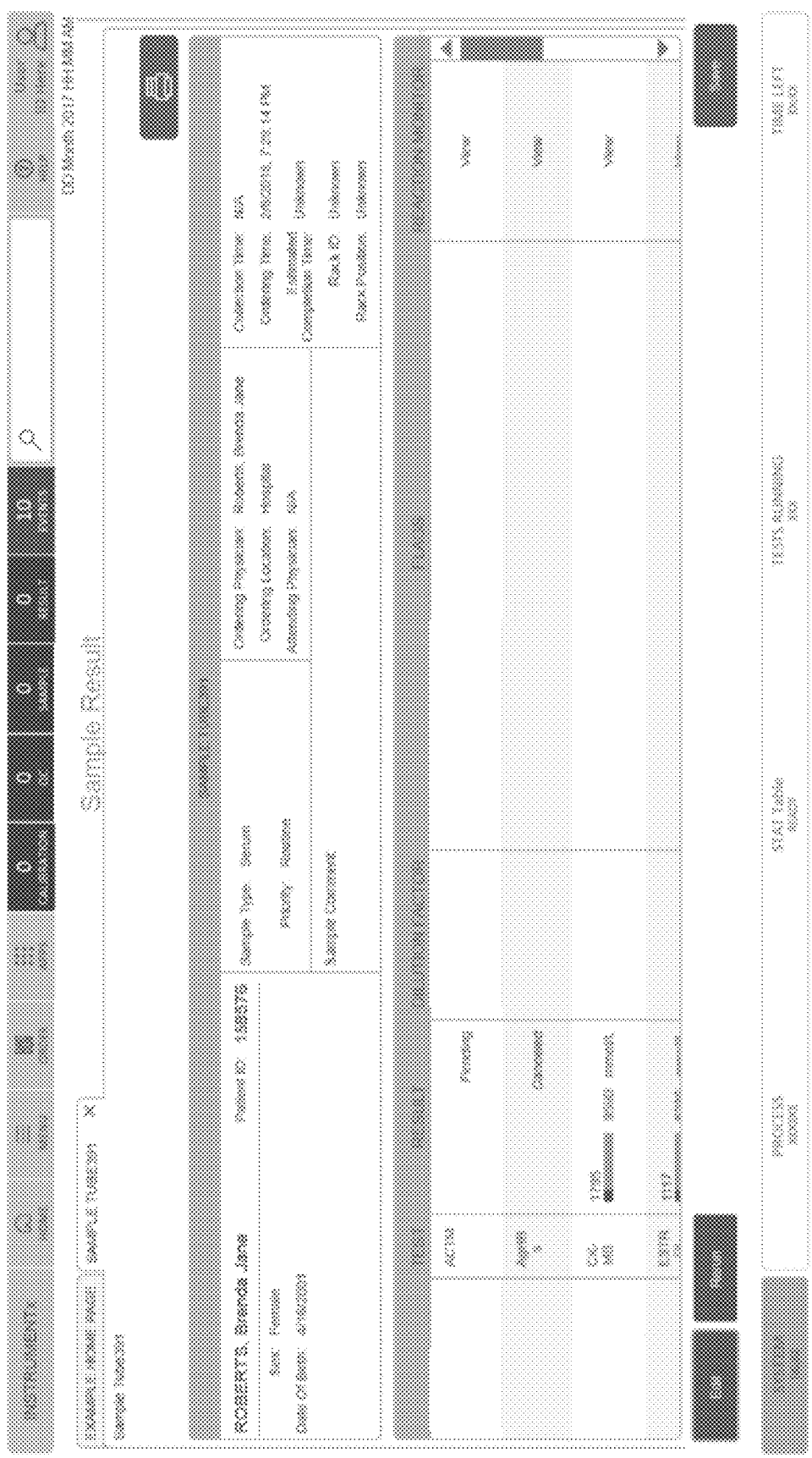
FIG. 5 illustrates an exemplary unmodified interface screen image.
Figure 6:
FIG. 6 illustrates an exemplary modified interface screen image such as could be created in some embodiments.
Figure 7:
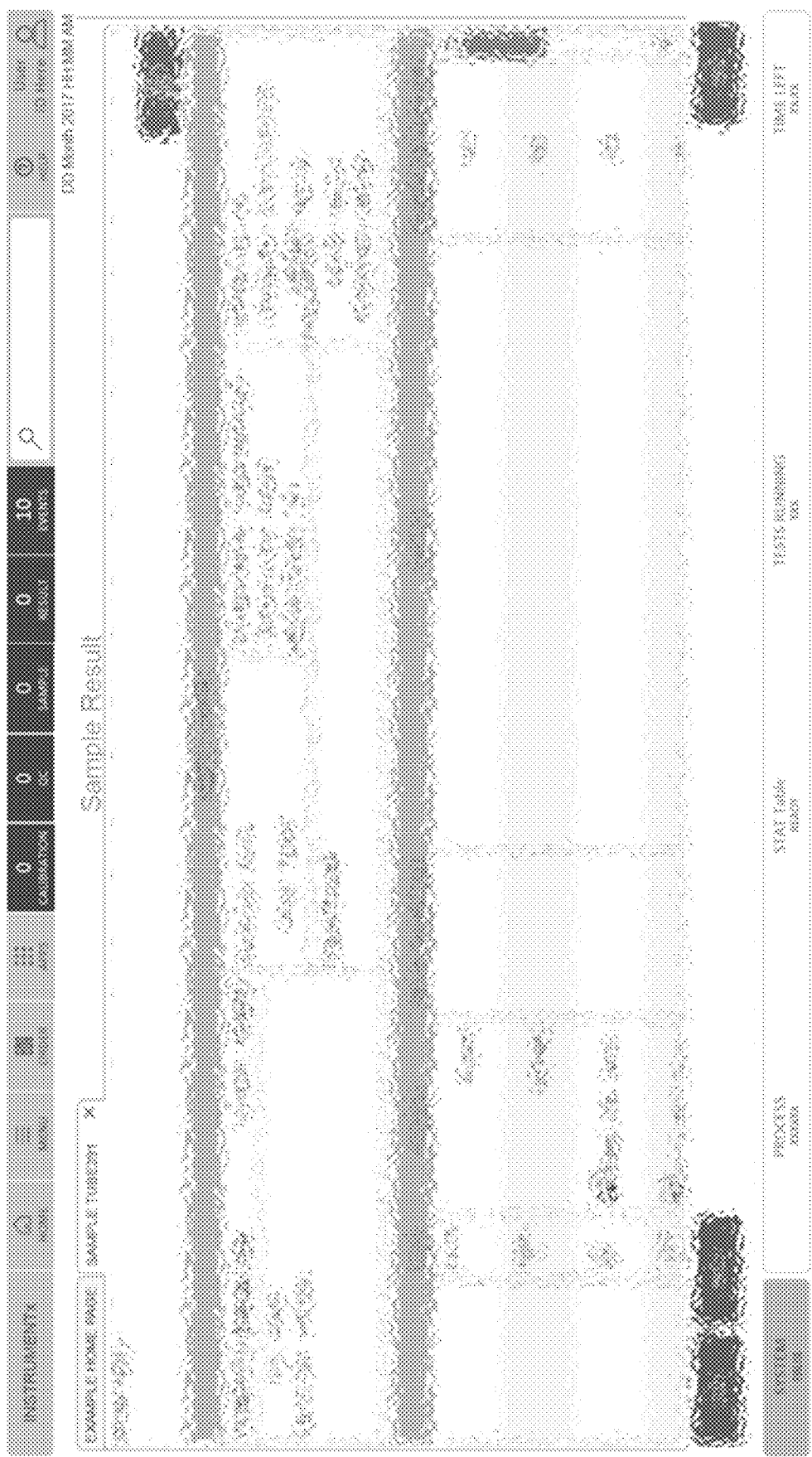
FIG. 7 illustrates an exemplary modified interface screen image such as could be created in some embodiments.

Of course, it should be understood that the advance configuration steps described above are also intended to be illustrative, and should not be treated as limiting. As an example of an alternative approach to advance configuration, consider the scenario in which instrumented safety glasses were provided by a manufacturer of laboratory instruments to assist the manufacturer in providing service to its customers during those instruments' operational lives. In such a scenario, the manufacturer might maintain a library of interfaces that would be presented by its machines, and when a pair of instrumented glasses captured an image of a machine, interfaces presented by the machine could be matched against the library. Then, when a match was found, the picture of the interface in a captured image could be overlaid with a generic interface image from the library or specific aspects of the interface in the captured image could be masked based on information in the library indicating locations in the relevant interface where confidential information would be displayed. An example of this type of selective masking is shown in FIGS. 5 and 6, where FIG. 5 illustrates an exemplary unmasked screen, and FIG. 6 illustrates information such as may be included in an interface library identifying portions of the screen that would be expected to include confidential information. Of course, it should be understood that the examples of FIGS. 5 and 6 are intended to be illustrative only, and should not be treated as limiting, and that other types of masking with other levels of selectivity, such as shown in FIG. 7, may also be used in some embodiments. Similarly, in some embodiments software controlling operation of a pair of instrumented safety glasses could be configured by a manufacturer to recognize that manufacturer's machines and screen out everything else in a captured image before sending it to a remote service provider.

As yet another variation, in some embodiments, this type of predefined interface library may be configurable and/or created by a user rather than by an instrument manufacturer. For example, a user may be provided with an interface through which he or she could upload examples of interfaces that would be displayed by instruments in his or her lab, and could then specify how those interfaces should be masked (e.g., by selecting one or more portions of the interface displaying information that can be used to identify, contact or locate an individual, or other confidential information; by specifying that the entire interface should be masked, etc.). Of course, it is also possible that, in some embodiments, a manufacturer could use this type of configuration interface as well, for example, to add interfaces presented by other manufacturers' machines to a predefined interface library. Accordingly, the preceding discussion of pre-configuration, like the discussion of the operation and components of a pair of instrumented glasses, should not be treated as implying limits on the scope of protection provided by this document or any other document claiming the benefit of this disclosure.

Another example of a type of variation which may be supported by some embodiments, is functionality that could be adapted for allowing aspects of the disclosed technology to be utilized by technicians that are local rather than remote relative to the relevant laboratory instrument. For example, to prevent confidential information from being inadvertently exposed to an onsite service technician, such a technician could be required to wear virtual reality headgear that would block out his or her vision and would replace it with a modified image generated in a manner such as described above so that he or she could still service the relevant machine without the risk of breaking confidentiality. Similarly, in some embodiments, aspects of the disclosed technology could be used to allow a remote technician to provide guidance to the operator of a laboratory instrument to enable him or her to perform service that would otherwise require the service of a specialized technician. For example, if the operator of a laboratory instrument was outfitted with augmented or virtual reality headgear, in some embodiments a remote service technician could be provided an interface that could allow him or her to highlight portions of a field of view image captured by the headgear, and that highlighting could then be presented to the operator (potentially as an overlay on an image that had been scrubbed of confidential information to match what was presented to the remote service technician, or as an overlay on the original image despite the fact that such image would be different from what was made available to the remote technician) as guidance to servicing the instrument. This type of approach could also be applied in contexts where virtual reality headgear is available, for example by displaying information that would otherwise be presented to a user of the laboratory instrument using augmented reality headgear to be presented instead (or in addition) on a display of the laboratory instrument itself, and/or on a display of a device proximate to the laboratory instrument (e.g., a tablet held by the operator, a local computer, etc.).

As another example of a type of alternative application of the disclosed technology, it is possible that images captured by a pair of instrumented glasses or other type of recording headgear could be saved and used as material for subsequent training and/or evaluation, with unnecessary material removed using approaches such as described previously so that such training and evaluation would not expose confidential information to those who should not have access to it. Accordingly, the discussion of using the disclosed technology to facilitate remote service while maintaining confidentiality should be understood as being illustrative only, and should not be treated as limiting.

Further variations on, features for, and potential implementations and applications of the inventors' technology will be apparent to, and could be practiced without undue experimentation by, those of ordinary skill in the art in light of this disclosure. Accordingly, neither this document, nor any document which claims the benefit of this document's disclosure, should be treated as being limited to the specific embodiments of the inventor's technology which are described herein.

As used herein, the singular forms "a", "an", and "the" include plural referents unless the context clearly dictates otherwise. The invention has now been described in detail for the purposes of clarity and understanding. However, it will be appreciated that certain changes and modifications may be practice within the scope of the appended claims.

As used herein, the term "based on" means that something is determined at least in part by the thing that it is indicated as being "based on." To indicate that something must be completely determined based on something else, it would be described as being based "exclusively" on whatever it is completely determined by.

As used herein, the term "camera" means a device for capturing and/or recording visual images. Examples of "cameras" include digital cameras that capture images using a charge coupled device and/or complementary metal-oxide-semiconductor sensor.

As used herein, a "computer" should be understood to refer to a group of devices (e.g., a device comprising a processor and a memory) capable of storing and executing instructions for performing one or more logical and/or physical operations on data to produce a result. A "computer" may include, for example, a single-core or multi-core microcontroller or microcomputer, a desktop, laptop or tablet computer, a smartphone, a server, or groups of the foregoing devices (e.g., a cluster of servers which are used in combination to perform operations on data for purposes such as redundancy and availability). In the claims, the word "server" should be understood as being a synonym for "computer," and the use of different words should be understood as intended to improve the readability of the claims, and not to imply that a "sever" is not a computer. Similarly, the various adjectives preceding the words "server" and "computer" in the claims are intended to improve readability, and should not be treated as limitations.

As used herein, the term "machine" refers to a device or combination of devices.

As used herein, "means for generating modified images which lack confidential information included in images captured by the head mounted camera" should be understood as a limitation set forth as a means for performing a specified function as provided for in 35 U.S.C. § 112(f), where the function is "generating modified images which lack confidential information included in images captured by the head mounted camera," and the corresponding structure is a computer configured as described in paragraphs 34 and 37-39, and depicted in FIG. 3.

As used herein, the term "network" refers to any collection of networks using standard protocols. For example, the term includes a collection of interconnected (public and/or private) networks that are linked together by a set of standard protocols (such as TCP/IP, HTTP, etc.) to form a global, distributed network. The term is also intended to encompass variations that may be made in the future, including changes and additions to existing standard protocols or integration with other media (e.g., television, radio, etc.).

As used herein, the term "sample" refers to any biological sample, and the phrase "biological sample" is meant to cover any specimen of biological material which has been isolated from its natural environment, such as the body of an animal or a human being. It can be in solid form such as tissues, bones, ligaments, and the like. It can also be in liquid form such as blood, spinal fluid, and the like.

As used herein, the term "set" refers to a number, group, or combination of zero or more things of similar nature, design, or function.

As used herein, modifiers such as "first," "second," and so forth are simply labels used to improve readability, and are not intended to imply any temporal or substantive difference between the items they modify. For example, referring to items as a "first program" and a "second program" in the claims should not be understood to indicate that the "first program" is created first, or that the two programs would necessarily cause different things to happen when executed by a computer. Similarly, when used in the claims, the words "computer" and "server" should be understood as being synonyms, with the different terms used to enhance the readability of the claims and not to imply any physical or functional difference between items referred to using those different terms.

As used herein, "laboratory" should be understood as a facility in which experiments or tests are performed on materials such as samples of biological materials collected from people or animals for purposes of medical diagnosis or treatment.

The invention claimed is:

1. A method comprising:
   a) capturing an image of a field of view of a head mounted camera;
   b) automatically generating, in near real time, a modified image by performing steps comprising:
      i) identifying one or more portions of the image of the field of view of the head mounted camera to be masked, wherein identifying one or more portions of the image of the field of view of the head mounted camera to be masked comprises:
         A) identifying one or more display screens in the field of view;
         B) for each of the one or more display screens, determining whether an interface is displayed on that display screen that matches an item from a predefined interface library; and
         C) for each displayed interface with at least one matching item from the predefined interface library, identifying one or more portions of that interface as portions of the image to be masked based on information from the matching item from the predefined interface library; and
      ii) masking each of the one or more identified portions; and
   c) presenting the modified image, wherein presenting the modified image comprises:
      i) displaying the modified image to a remote service technician; or
      ii) displaying the modified image on a display of an augmented reality headpiece wherein the head mounted camera is integrated with the augmented reality headpiece;
   wherein:
   A) the field of view of the head mounted camera is a view of a laboratory comprising one or more laboratory instruments for analyzing patient samples;
   B) the predefined interface library is a library comprising interfaces which are adapted to display confidential information related to the patient samples at fixed interface locations; and
   C) masking each of the one or more identified portions comprises, for each displayed interface with at least one matching item from the predefined interface library, masking the fixed interface locations at which that interface is adapted to display confidential information related to the patient samples.

2. The method of claim 1, wherein masking each of the one or more identified portions comprises, for each interface displayed on one of the one or more display screens having at least one matching item from the predefined interface library, overlaying an image corresponding to that interface from the predefined interface library.

3. The method of claim 1, wherein:
   a) the method comprises, prior to capturing the image of the field of view of the head mounted camera, providing one or more notation media exemplar images;
   b) identifying one or more portions of the image of the field of view of the head mounted camera to be masked comprises:
      i) identifying one or more notation media in the field of view based on information from the notation media exemplar images; and
      ii) identifying each of the one or more notation media in the field of view as one of the one or more portions of the image of the field of view of the head mounted camera to be masked.

4. The method of claim 1, wherein:
   a) presenting the modified image comprises transmitting the modified image to the remote service technician;
   b) the method comprises:
      i) prior to capturing the image of the field of view of the head mounted camera, specifying an imageable area of a laboratory;
      ii) determining, after capturing the image of the field of view of the head mounted camera, and based on one or more wireless transceivers located at a border of the imageable area, whether the head mounted camera is located in the imageable area of the laboratory; and
      iii) based on a determination that the head mounted camera is not located in the imageable area of the laboratory, automatically deactivating transmission functionality of the head mounted camera.

5. The method of claim 1, wherein the transmission functionality of the head mounted camera is automatically deactivated by automatically deactivating the head mounted camera.

6. The method of claim 1, wherein:
   a) presenting the modified image comprises displaying the modified image to the remote technician;

b) the method comprises:
   i) prior to capturing the image of the field of view of the head mounted camera, specifying an imageable area of a laboratory;
   ii) determining, after capturing the image of the field of view of the head mounted camera, and based on distance from a wireless transceiver located inside of the imageable area, whether the head mounted camera is located in the imageable area of the laboratory; and
   iii) based on a determination that the head mounted camera is not located in the imageable area of the laboratory, automatically deactivating transmission functionality of the head mounted camera.

7. The method of claim 1, wherein:
a) presenting the modified image comprises displaying the modified image to the remote service technician; and
b) the method comprises transmitting the modified image to the remote service technician using an internet connection.

8. The method of claim 1, wherein:
a) presenting the modified image comprises displaying the modified image to the remote service technician;
b) the method comprises, simultaneously with displaying the modified image to the remote service technician, displaying the image of the field of view of the head mounted camera on the display of the augmented reality headpiece wherein the head mounted camera is integrated with the augmented reality headpiece.

9. The method of claim 1, wherein:
a) the image is captured as part of a video stream;
b) the method comprises transmitting the modified image to the remote service technician; and
c) transmitting the modified image to the remote service technician is performed by transmitting a version of the video stream that includes the modified image rather than the captured image.

10. The method of claim 1, wherein the image of the field of view of the head mounted camera includes confidential information outside of the one or more portions identified as portions to be masked.

11. The method of claim 1, wherein the head mounted camera is comprised by a pair of instrumented safety glasses.

12. The method of claim 1, wherein:
a) presenting the modified image comprises displaying the modified image to the remote technician;
b) the method comprises:
   i) the remote technician generating, based on the modified image, a remediation overlay comprising information for addressing a problem in a laboratory instrument in the field of view of the head mounted camera; and
   ii) displaying an image comprising the remediation overlay on a display of the laboratory instrument.

13. The method of claim 1, wherein masking each of the one or more identified portions comprises, for each interface displayed on one of the one or more display screens having at least one matching item from the predefined interface library, masking portions of that interface at locations indicated by the at least one matching item in the predefined interface library.

14. A system comprising:
a) a head mounted camera;
b) a processor;

wherein:
i) the processor is configured with a set of computer instructions operable to, when executed:
   A) after the head mounted camera has been activated, determine whether modified images based on images captured by the head mounted camera should be made available for non-immediate viewing;
   B) both create a modified image based on an image captured by the head mounted camera and make the modified image available for non-immediate viewing if and only if:
      I) a determination is made that the modified image should be made available for non-immediate viewing; and/or
      II) both of the following statements are true:
         1) a determination was made that modified images based on images captured by the head mounted camera should be made available for non-immediate viewing prior to the image captured by the head mounted camera being captured; and
         2) no determination was made that modified images based on images captured by the head mounted camera should not be made available for non-immediate viewing more recently than the most recent determination that modified images based on images captured by the head mounted camera should be made available for non-immediate viewing;
ii) creating the modified image based on the image captured by the head mounted camera comprises:
   A) identifying one or more portions of the image captured by the head mounted camera to be masked by performing acts comprising:
      I) identifying one ormore display screens in the image captured by the head mounted camera;
      II) for each of the one or more display screens, determining whether an interface is displayed on that display screen that matches an item from a predefined interface library; and
      III) for each displayed interface with at least one matching item from the predefined interface library, identifying one or more portions of that interface as portions of the image to be masked based on information from the matching item from the predefined interface library; and
   B) masking each of the one or more identified portions;
iii) the field of view of the head mounted camera is a view of a laboratory comprising one or more laboratory instruments for analyzing patient samples;
iv) the predefined interface library is a library comprising interfaces which are adapted to display confidential information related to the patient samples at fixed interface locations; and
v) masking each of the one or more identified portions comprises, for each displayed interface with at least one matching item from the predefined interface library, masking the fixed interface locations at which that interface is adapted to display confidential information related to the patient samples.

15. The system of claim 14, wherein the computer instructions are operable to, when executed, determine whether images captured by the head mounted camera should be made available for non-immediate viewing by performing a set of steps comprising:
a) determining if the head mounted camera is located within a predefined area; and b) based on a determination that the head mounted camera is not located within the predefined area, determining that images captured by the head mounted camera should not be made available for non-immediate viewing.

16. The system of claim 15, wherein:
a) the system comprises one or more wireless transceivers located at a border of the predefined area; and
b) the determination that the head mounted camera is not located within the predefined area is based on detection of the head mounted camera crossing the border of the predefined area.

17. The system of claim 14, wherein
a) the system comprises a laboratory instrument;
b) the computer instructions are operable to, when executed, determine whether images captured by the head mounted camera should be made available for non-immediate viewing by performing a set of steps comprising:
  i) determining an orientation of the head mounted camera relative to the laboratory instrument; and
  ii) based on a determination that the orientation of the head mounted camera is offset from the laboratory instrument by 90 degrees or more, determining that images captured by the head mounted camera should not be made available for non-immediate viewing.

18. The system of claim 14, wherein the system comprises a laboratory instrument configured to encrypt images captured by the head mounted camera.

19. The system of claim 14, wherein:
a) the head mounted camera comprises an exterior light source;
b) the head mounted camera is configured to activate the exterior light source when the head mounted camera is activated and when a determination is made that images captured by the head mounted camera should be made available for non-immediate viewing; and
c) the head mounted camera is configured to deactivate the exterior light source when the head mounted camera is deactivated and when a determination is made that images captured by the head mounted camera should not be made available for non-immediate viewing.

* * * * *